(12) United States Patent
Steiner et al.

(10) Patent No.: US 11,273,059 B2
(45) Date of Patent: Mar. 15, 2022

(54) PROSTHESIS FOR FEMORAL AMPUTEE

(71) Applicant: S & S Sàrl, Moutier (CH)

(72) Inventors: Jean-Louis Steiner, Moutier (CH); Clément Schneider, Le Landeron (CH)

(73) Assignee: S & S SÀRL, Moutier (CH)

( * ) Notice: Subject to any disclaimer, the term of this patent is extended or adjusted under 35 U.S.C. 154(b) by 114 days.

(21) Appl. No.: 16/618,150

(22) PCT Filed: May 31, 2017

(86) PCT No.: PCT/EP2017/063181
§ 371 (c)(1),
(2) Date: Nov. 28, 2019

(87) PCT Pub. No.: WO2018/219450
PCT Pub. Date: Dec. 6, 2018

(65) Prior Publication Data
US 2020/0163780 A1    May 28, 2020

(51) Int. Cl.
*A61F 2/64* (2006.01)
*A61F 2/74* (2006.01)
*A61F 2/68* (2006.01)
*A61F 2/50* (2006.01)
(Continued)

(52) U.S. Cl.
CPC ................ *A61F 2/64* (2013.01); *A61F 2/68* (2013.01); *A61F 2/74* (2021.08);
(Continued)

(58) Field of Classification Search
None
See application file for complete search history.

(56) References Cited

U.S. PATENT DOCUMENTS 2,327,042 A * 8/1943 Hinkle ............... A61F 2/64
623/44
2,561,370 A * 7/1951 Henschke ........... A61F 2/68
623/26
(Continued)

FOREIGN PATENT DOCUMENTS

EP    0 056 602 A1 *  7/1982  ............. A61F 2/68
EP    2015711 A1       1/2009
(Continued)

OTHER PUBLICATIONS

Mauch, Hans. "Stance Control for Above-Knee Artificial Legs—Design Considerations in the S-N-S Knee." Bulletin of Prosthetics Research. Fall 1968. 12 pages.
(Continued)

*Primary Examiner* — David H Willse
(74) *Attorney, Agent, or Firm* — Pearne & Gordon LLP

(57) ABSTRACT

A hinged connecting device comprising a damping mechanism intended to counter a predetermined resistance at least during bending of the prosthesis (1), by replacing the muscle groups usually used for this purpose. The damping mechanism (200) is capable of being switched between a first operating mode (M1), selected by default, in which the value of the resistance corresponds to a first maximum value (Vmax), and a second operating mode (M2), that can be actuated only in a hyperextension position (P0) of the prosthesis (1), in which the resistance value corresponds to a second minimum value (Vmin); and the hinged connecting device (2) moreover comprises a fully mechanical locking system (3), arranged in order to allow the second operating mode (M2) to be activated only when the inclination of the tibial part (102) exceeds a first predetermined oriented angle (X1) relative to the vertical.

13 Claims, 7 Drawing Sheets

(51) Int. Cl.
A61F 2/60 (2006.01)
A61F 2/66 (2006.01)
A61F 2/76 (2006.01)

(52) U.S. Cl.
CPC ........... *A61F 2002/5006* (2013.01); *A61F 2002/5018* (2013.01); *A61F 2002/5021* (2013.01); *A61F 2002/5038* (2013.01); *A61F 2002/607* (2013.01); *A61F 2002/608* (2013.01); *A61F 2002/6614* (2013.01); *A61F 2002/6836* (2013.01); *A61F 2002/6854* (2013.01); *A61F 2002/7625* (2013.01)

(56) References Cited

U.S. PATENT DOCUMENTS

| | | |
|---|---|---|
| 6,159,248 A | 12/2000 | Gramnas |
| 2003/0125814 A1 | 7/2003 | Paasivaara et al. |
| 2011/0307078 A1* | 12/2011 | Boender ............... F16F 9/512 |
| | | 623/26 |

FOREIGN PATENT DOCUMENTS

| | | | |
|---|---|---|---|
| EP | 2730256 A1 | 5/2014 | |
| JP | H01274758 A * | 11/1989 | ............... A61F 2/64 |

OTHER PUBLICATIONS

International Search Report and Written Opinion in PCT/EP2017/063181 dated Feb. 20, 2018, 13 pages.

* cited by examiner

PROSTHESIS FOR FEMORAL AMPUTEE

TECHNICAL FIELD OF THE INVENTION

This invention relates to the field of knee prostheses for a femoral amputee, and more specifically to fully mechanical knee prostheses, that is to say devoid of any sensor or electronic control system.

STATE OF THE ART

In order to make it possible to simulate at best the articulation of a healthy knee, recent developments have sought to provide prostheses with sophisticated integrated electronic systems to determine and control the flexion of the tibial part with respect to the femoral part, based on position and acceleration data obtained from various sensors. One drawback of this type of solution is that it requires especially efficient processors to process the sensor data and implement relatively complex algorithms designed to ensure the stability of the wearer, all the while reproducing the most natural possible movement of the leg. Firstly, this type of solution turns out to be particularly cumbersome to systematically ensure a sufficiently short reaction time of the system; moreover, it consumes an appreciable amount of energy and requires a frequent replacement or recharging of electrical batteries intended to supply the system; lastly, any electronic failure could prove catastrophic for the prosthesis wearer.

Since the end of the 1960s, however, other types of prostheses have been known moreover which, in contrast, are fully mechanical, that is to say they do not require the use of any sensor or electronic system, and all the more so do not need any supply of electrical energy. These prostheses, using essentially a preferably hydraulic piston simulating the group of muscles associated in particular with the quadriceps, are often referred to as "swing & stance" prostheses, because they operate alternatively based on a so-called "stance" mode where the resistance to the flexion is high—and a "swing" mode, where the resistance to the flexion is reduced and the leg can thus more easily bend, for example when a step is taken, following the phase in which the leg is pushed and then brought forward. As explained in the scientific article: Mauch—Stance Control for AK Prosthesis, Bulletin of Prosthetics Research/Fall 1968, except for a voluntary blockage by the user in the stance mode of the prosthesis to avoid any disequilibrium, there exist several control mechanisms managing their alternating activation automatically in the context of normal movement, and notably the one based on the detection of the placement of the heel, referred to as "heel-control", with a non-stance mode as the default, another based on the flexion of the foot and/or the detection of pressure on the front of the foot, called "toe-control", with a stance mode as default, and finally one detecting the application of a compression force on the prosthesis, referred to as "weight control", whose mode of operation is relatively close to that of the "heel control". None of these mechanisms has been shown to be suitable, however, for descending stairs, which renders their use not very practical.

In order to alleviate this problem and improve comfort of use in the greatest number of real-life situations possible, including walking down stairs, another system, the so-called "hyperextension control" system has been proposed. This control mechanism is stance mode by default when a weight is applied on the prosthesis corresponding to the placing of the heel on the ground, but activates the swing phase when the leg is fully extended, namely when the tibial part is substantially aligned with the femoral part of the prosthesis. In other words, an unblocking making it possible for the leg to bend more easily is supposed to be theoretically possible at the end of the phase of pushing on the leg, but never at any other time. A re-extension of the leg is moreover permitted to carry out the normal swing motion of the tibial part of the leg, when a step is taken starting from a slightly bent position at the moment where the foot is no longer supported on the ground, thanks to the action of a valve which is intended to close only when weight is applied on the prosthesis and is therefore in an open position at that moment.

A drawback of this type of above-described prosthesis is that there exists however a risk of unblocking of the stance mode during an involuntary extension of the leg and which would risk in this case a fall.

Thus there exists a need for a solution without these known limitations.

SUMMARY OF INVENTION

One object of the present invention is to propose a prosthesis whose reliability is improved, all while keeping production and labor costs reduced.

According to the invention, these objects are achieved by means of a hinged connecting device for a prosthesis for a femoral amputee, and in particular a fully mechanical locking system, designed to permit the activation of the second operating mode—where the value of the resistance corresponds to a second minimal value, as opposed to the value of maximal resistance of the first mode of operation—only from a certain inclination of the said tibial part corresponding to a first predetermined oriented angle with respect to the vertical in the direction of walking.

An advantage of the proposed solution is that it provides a prosthesis which is not limited in terms of scenarios of use for everyday life and thus substitutes efficiently for the groups of muscles to be replaced or respectively emulated by the prosthesis.

Another advantage of the proposed solution is that it provides in parallel increased safety in terms of stability, notably when the heel strikes the ground when a step is taken, and more generally in any situation of potential disequilibrium of the wearer of the prosthesis.

Still another advantage of the proposed solution is that it provides, according to a preferred embodiment, a prosthesis of simple and modular construction, easily adaptable to the majority of existing pistons provided for prostheses of the "swing and stance" (SNS) type, without necessitating moreover structural modifications or important additional accommodations on the prosthesis.

According to a preferred embodiment, the secured switching device is furthermore adjustable, with a view to being adapted optimally to the movement of the wearer of the prosthesis and thus optimally ensuring stability when the heel strikes the ground.

BRIEF DESCRIPTION OF DRAWINGS

Other advantageous features will follow more clearly from the description which follows of a particular embodiment of the invention, given by way of non-limiting example, and represented by the attached drawings in which.

DETAILLED DESCRIPTION

Figure 1:
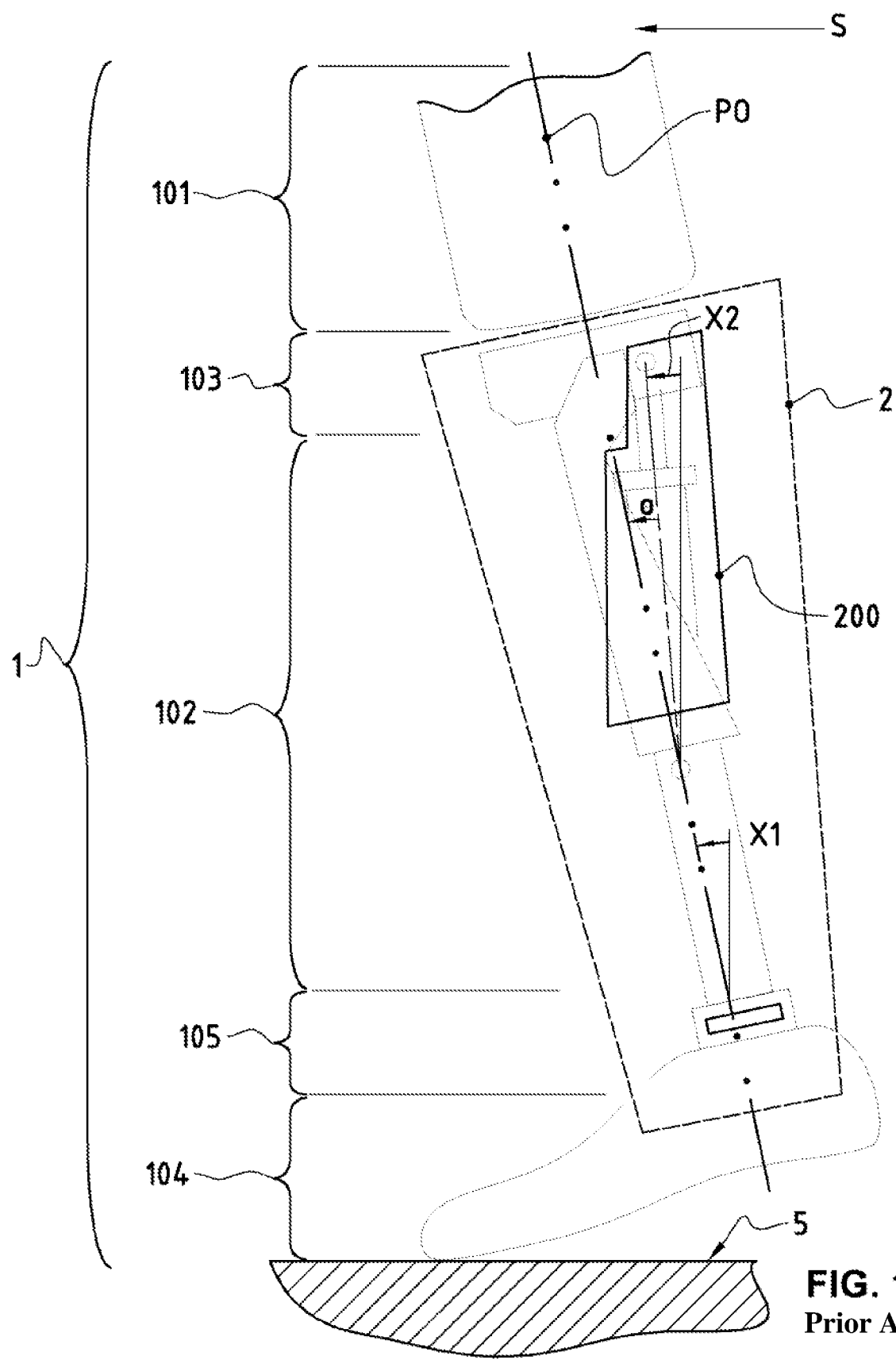
FIG. 1 shows a prosthesis known from the prior art.

FIG. 1 is a profile view of a swing and stance type prosthesis which will be referred to from now on simply as an "SNS" prosthesis.

The prosthesis 1 conventionally comprises a femoral part 101, ending the thigh, and intended to be adjusted on the stump of the amputee, as well as a tibial part 102 replacing the amputee's leg, and a foot part 104 replacing the amputee's foot, with a view to ensure taking support on a support surface 5, typically the ground or floor. So as to ensure an articulated connection between the femoral part 101 and the tibial part 102 of the prosthesis, the intermediate knee part 103 which connects them comprises a hinged connecting device 2 simulating this articulation by providing a degree of freedom in limited rotation between a first position P0 of hyperextension, in which the femoral part 101 and the tibial part 102 extend substantially in the prolongation one from the other, and a second position P1 of maximal flexion, illustrated further on in FIG. 3, in which the femoral part 101 and the tibial part 102 form a predefined maximal flexion angle. The hinged connecting device 2 is moreover of asymmetrical design, just like a healthy knee, and a flexion is only possible in a single given direction of rotation.

The prosthesis 1 represented in FIG. 1 also potentially comprises an articulation of ankle type 105 between the foot part 104 and the tibial part 102; nevertheless the hinged connecting device 2 according to the present invention, described in the following, does not require any such articulation at the foot and would also function with a prosthesis 1 devoid thereof.

The hinged connecting device 2 of the prosthesis comprises moreover a damping mechanism 200, taking here the form of a piston, intended to counter a predetermined and variable resistance for the prosthesis 1, with a view to replacing the thigh and the leg of the amputee in as realistic a way as possible, all the while ensuring systematically the stability of the wearer of the prosthesis whenever weight is applied thereon. To that end, the piston is capable of being switched between a first operating mode M1, selected by default, in which the value of the resistance is fixed at a first maximal value (Vmax), which consequently corresponds to the mode referred to as "stance", and a second operating mode M2, in which the value of resistance is fixed to a second minimal value (Vmin), and which consequently corresponds to the mode referred to as "swing", which is only supposed to be able to be actuated in the first position P0 of hyperextension, in which the prosthesis is represented in FIG. 1. In this figure, the prosthesis is furthermore represented supported on the front part of the foot 104, that is to say just before this foot leaves the floor when a step is taken. The prosthesis 1 is thus slightly inclined forward, and the angle formed between the tibial part 102 of the prosthesis 1 and the vertical forms a predetermined oriented angle X1 greater than or equal to 0 in the direction of walking S, which corresponds to the sum of the second predetermined oriented angle X2 formed between the piston and the vertical and the angle between the piston and the tibial part Θ, usually of a few degrees, at most 5 to 10 degrees.

A major objective of the present invention is to allow the switching from the first operating mode M1 to the second operating mode M2 of such a prosthesis 1 only in a situation corresponding to that illustrated schematically by FIG. 1, that is to say in a situation where the prosthesis 1 is definitely situated in hyperextension, but where the leg is also slightly inclined forward in the direction of walking S, and this in order to preemptively prevent any premature activation of the swing mode, notable when the heel strikes the ground or even during a backward imbalance of the wearer of the prosthesis. The sequence of execution of a step with a prosthesis 1 equipped with an articulated connecting device 2 according to the invention is described by the series of FIGS. 4A,4B,4C,4D.

Figure 2:
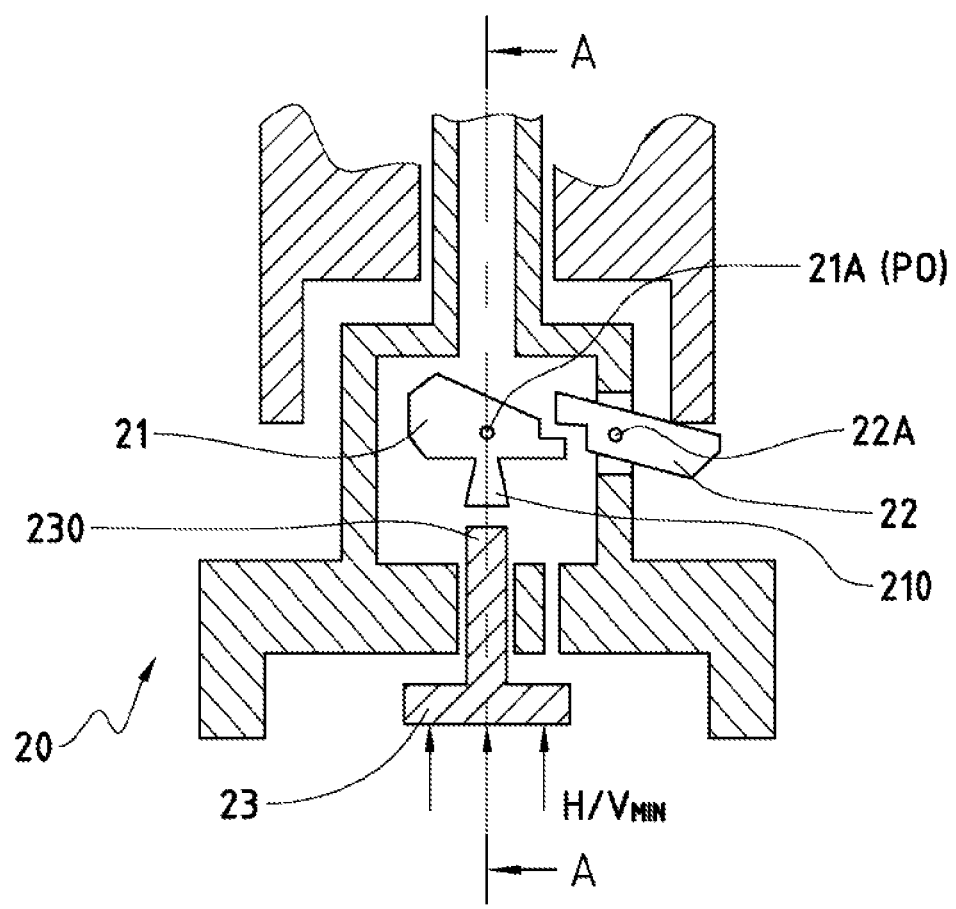
FIG. 2 shows the detail of the mechanism for control of the valve of the piston of such a prosthesis, according to the prior art.

FIG. 2 illustrates a standard switching system 20 implemented in the piston of an SNS prosthesis 1 for the passage from the stance mode to the swing mode, that is to say from the first operating mode M1, selected by default, to the second operating mode M2. The piston comprises, mounted pivoting on its axis 21A disposed on the axis A-A of the piston, a pendulum 21, which serves as a check valve for the valve 23 during the swing mode (in which the piston is represented in this figure) thanks to the stop portion 210 which co-operates on the rod 230 of the valve 23. When the prosthesis is in the first position of P0 of hyperextension, a force F is exerted by a protruding portion on the edge of the piston, and tips the counterweight 22, mounted in a way pivoting about its axis 22A, offset with respect to the axis A-A of the piston, which thus frees the pendulum 21, previously retained and by default in a locked position, allowing the closing of valve 23, ensuring maximal resistance. The position of the pendulum 21, vertically suspended but henceforth not blocked by the counterweight 22, is such that the resistance of the damping mechanism 200 formed by the piston is switched to a minimal value Vmin, because despite the hydraulic pressure H exerted on the valve 23, in the direction of the arrows pointing upward from below (owing to the weight exerted on the prosthesis), the latter can no longer close and the passage of the fluid at the orifices normally blocked by the valve 230 in stance mode decreases by as much as the resistance exerted by the damping mechanism 200.

Figure 3:
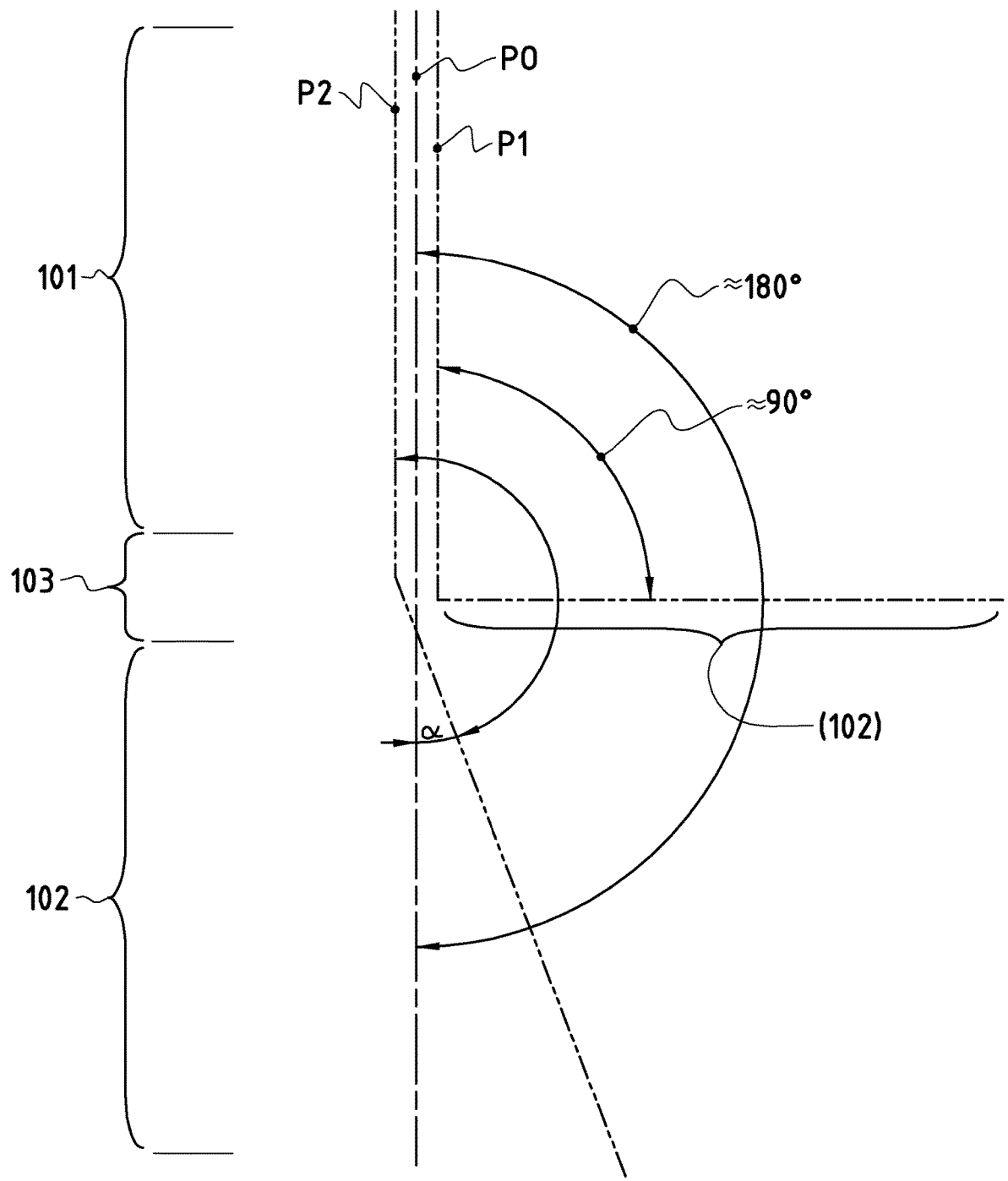
FIG. 3 shows a basic diagram showing the different possible configurations for the prosthesis.

FIG. 3 illustrates schematically the different parts of a prosthesis as well as the different relative angles between the femoral part 101 and the tibial part 102 of the prosthesis around the knee part 103 intended to replace this joint. As can be seen in this figure, in the first position of hyperextension P0, the angle between the tibial part 102 and the femoral part 103 is flat, that is to say substantially equal to 180 degrees. In practice, based on the models, the angle between these two parts could deviate slightly, by being preferably slightly greater by a few degrees at this flat angle in hyperextension position such that the wearer of the prosthesis 1 could easily tell that the latter was in hinge position permitting the unblocking of the stance mode, that is to say permitting the switching to the swing mode.

FIG. 3 shows furthermore schematically the second bent position P1 of the prosthesis, here according to a maximal flexion angle of about 90 degrees; however, this angle can be adjusted according to the needs. Nevertheless a third intermediate position P2 can be noted, which deviates slightly, by α few degrees, from the first position of extension. The angular differential a between these two positions, that is to say the first position of hyperextension P0 and the third intermediate position P2, is ordinarily a few degrees at most, and this angular course corresponds to the additional advancement of the piston once a threshold resistance due to a spring, typically a Belleville spring, has been surpassed, thus permitting the force F of FIG. 2 to be exerted on the peripheral part of the counterweight 22 in order to tilt it and release the pendulum 21. In other words, the magnitude of the force F must surpass a predetermined threshold inherent to this spring, which causes moreover a "click" effect allowing the user to determine whether the second operating mode M2 of swing is able to be activated or not.

In the following, reference will be made to the series of FIGS. 4A-4D which illustrate different positions and configurations of a prosthesis 1 modified according to a preferred embodiment of the invention when a step is taken. Although these stages are supposed to come as close as possible to what occurs theoretically with a healthy knee, it could however be noted that the sequence is slightly modified since it is necessary to manage a switching stage between the different resistance modes, whereas the muscular group of quadriceps allow managing this resistance in continuous fashion. Furthermore, since all the reference numerals or symbols relating to the various constituent elements of the schematically illustrated prosthesis 1 are identical, they will not be dealt with in detail for each of these figures.

Figure 4A:
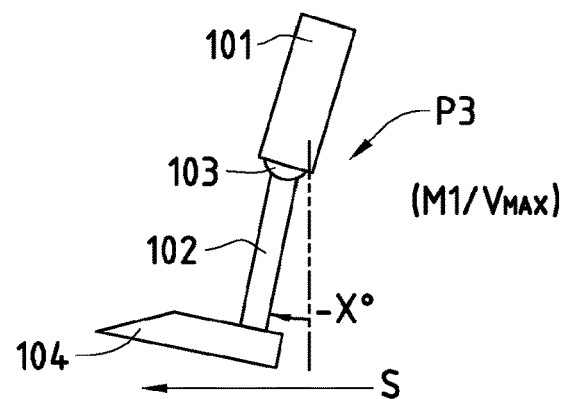
FIG. 4A shows a schematic view of a prosthesis according to the invention, in a first operating position, in stance mode.

FIG. 4A shows the first stage carried out during a step, that is to say when the heel of the foot touches the ground. In this configuration, the tibial part 102 forms an oriented angle of $-x°$ with respect to the vertical, and only the rear of the foot part 104 rests on the ground, whereas the femoral part 101 is still not completely aligned on the tibial part 102 at the articulation formed by the knee part 103. The prosthesis 1 is thus typically in the third intermediate position P3, in which the second operating mode M2 of swing is still not able to be activated.

Then, as illustrated in the following FIG. 4B, by resting on the heel of the prosthesis 1, one can pass into the first position of hyperextension P0 by exerting a slight pressure rearwards of the stump of the thigh, in the direction opposite the direction of walking S, thus making switching to the swing mode possible. The angle of the tibial part 102 in relation to the ground has not changed and still forms an oriented angle of $-x°$ with respect to the vertical. In such a configuration, even though the second operating mode of swing M2 is theoretically able to be activated by reason of the position of hyperextension P0 in which the prosthesis 1 is situated, no switching is possible because of the locking system 3 described further on in relation to FIGS. 5 to 7.

Then, as illustrated in the following FIG. 4C, the prosthesis 1 is still in the first position of hyperextension P0, but it is tipped, in its entirety, forwards in the direction of walking S, while the foot part 104 is completely placed on the ground, such that the angle between the tibial part 102 and the vertical with respect to the ground is brought back to about 0 degrees. Because of the locking system 3, the switching from the stance mode to the swing mode is still inoperative.

Figure 4B:
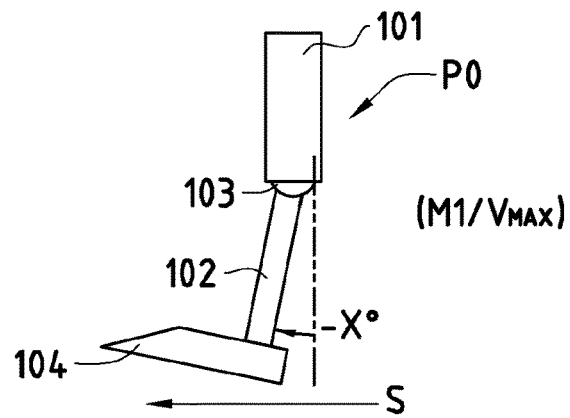
FIG. 4B shows a schematic view of a prosthesis according to the invention, in a second operating position, still in stance mode.
Figure 4C:
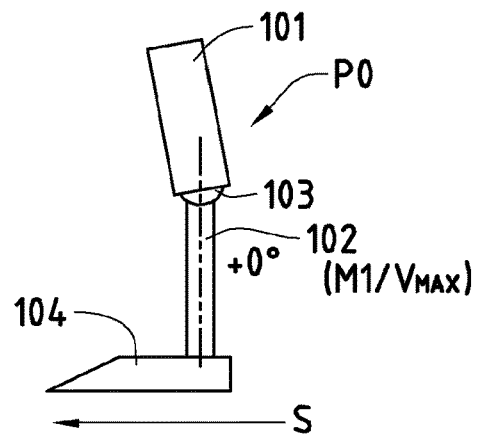
FIG. 4C shows a schematic view of a prosthesis according to the invention, in a fourth operating position, once again in stance mode.
Figure 4D:
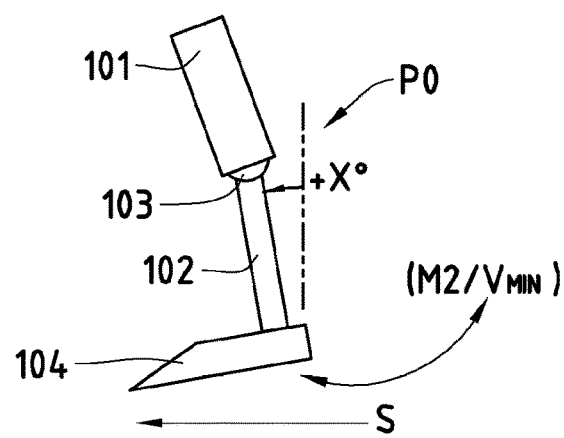
FIG. 4D shows a schematic view of a prosthesis according to the invention, in a fifth operating position, in which the stance mode has been switched to the swing mode.

It is only during the last sequence illustrated in FIG. 4D that switching will be possible. The prosthesis 1 is again still in the first position of hyperextension P0, but continues to tip forwards in the direction of walking S, such that from now on only the tip of the toe of the foot is supported on the ground and the angle between the tibial part 102 and the vertical in relation to the ground exceeds a positive angle of $+x°$ degrees with respect to the vertical. Only starting from this moment here is the switching from the first stance mode, (where the resistance of the damping device 200 constituted by the piston is maximal (value Vmax)), possible to the second operating mode M2 (where the resistance of the piston is minimal (value Vmin)), and the tibial part 102 can swing rearwards.

Thus, the locking device 3 makes it possible to ensure that in the configuration illustrated by FIGS. 4B and 4C, constituting the intermediate stages following the striking of the heel on the ground, no dysfunction is able to take place from now on in terms of untimely switching of the prosthesis from one operating mode to the other, whereas according to the known prostheses of the prior art, such an inconvenience could occur, depending on the wearer and the moment at which the hyperextension was triggered, since no locking or respectively unlocking device has been available to provide additional safety of use. Furthermore, even during a disequilibrium of the wearer of the prosthesis 1 rearwards and the involuntary unblocking of the counterweight by passing into the first position of hyperextension P0, no switching into the swing mode will be possible.

Thus, according to the invention, additional safety is provided with respect to existing prostheses, the possibility of switching from one operating mode to the other being made conditional upon the value of the angle which the tibial part 102 forms in relation to the vertical. In the following, several variants will be described, illustrated in particular by FIGS. 5 to 7, relating to a preferred embodiment for achieving the locking device 3 according to the invention, which is incorporated in a piston serving as damping mechanism 200, and involving a modified pendulum whose center of gravity is offset with respect to the axis of this piston to constitute a modified switching system. Such a variant involves only a minimum of structural modifications with respect to an existing SNS prosthesis and greatly facilitates the implementation of the locking system 3, without necessitating the addition of a supplementary dedicated system fulfilling the new condition of safety sought. The ergonomics of the prosthesis is moreover not affected, no special accommodation being required outside the piston, which minimizes moreover the constraints in terms of the volume required.

Figure 5:
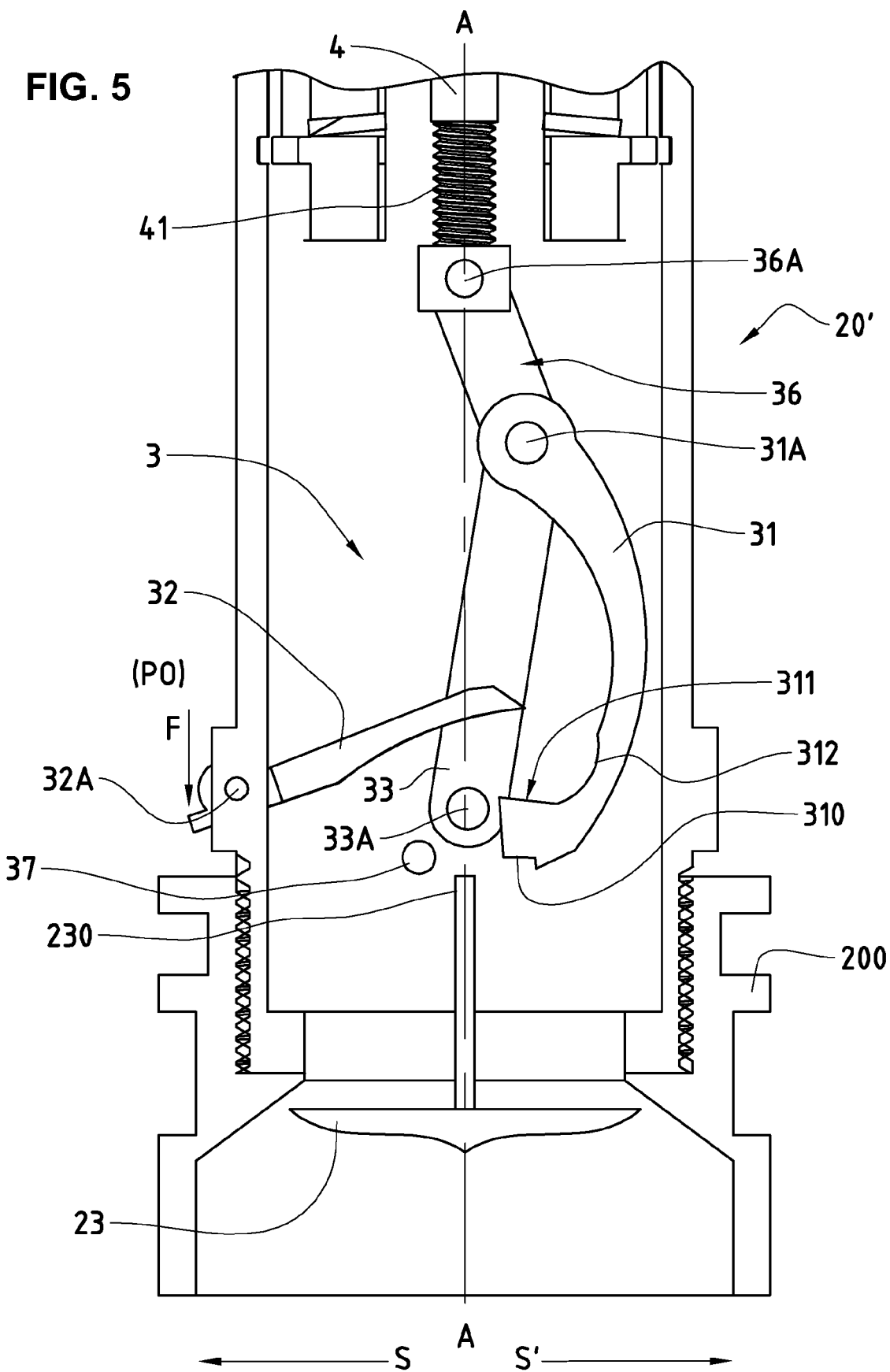
FIG. 5 is a sectional view of a modified pendulum for the switching between the stance mode and the swing mode of the prosthesis according to a first preferred embodiment of the invention.
Figure 6:
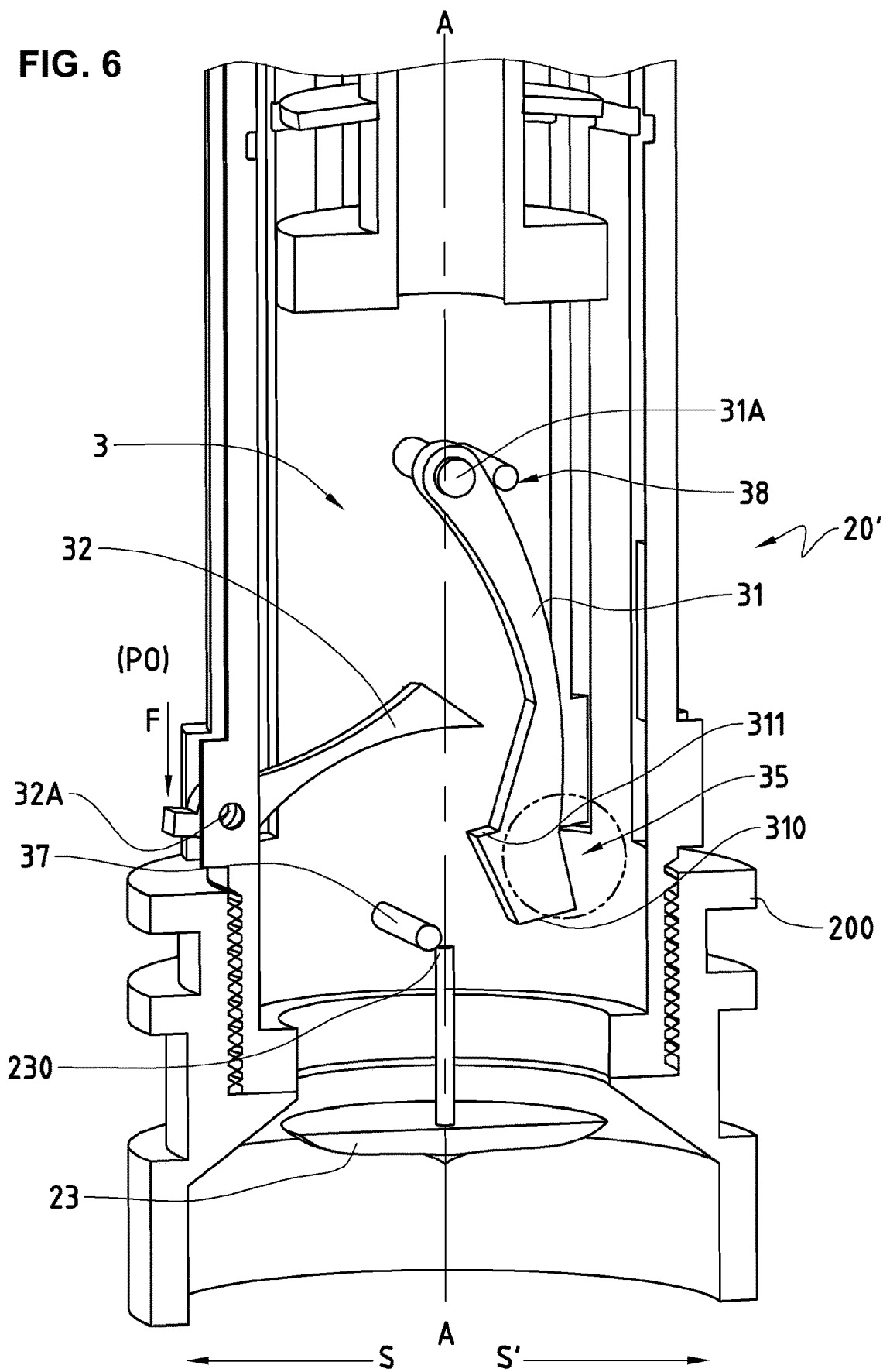
FIG. 6 is a sectional view of a modified pendulum for the switching between the stance mode and the swing mode of the prosthesis according to a second preferred embodiment of the invention.
Figure 7:
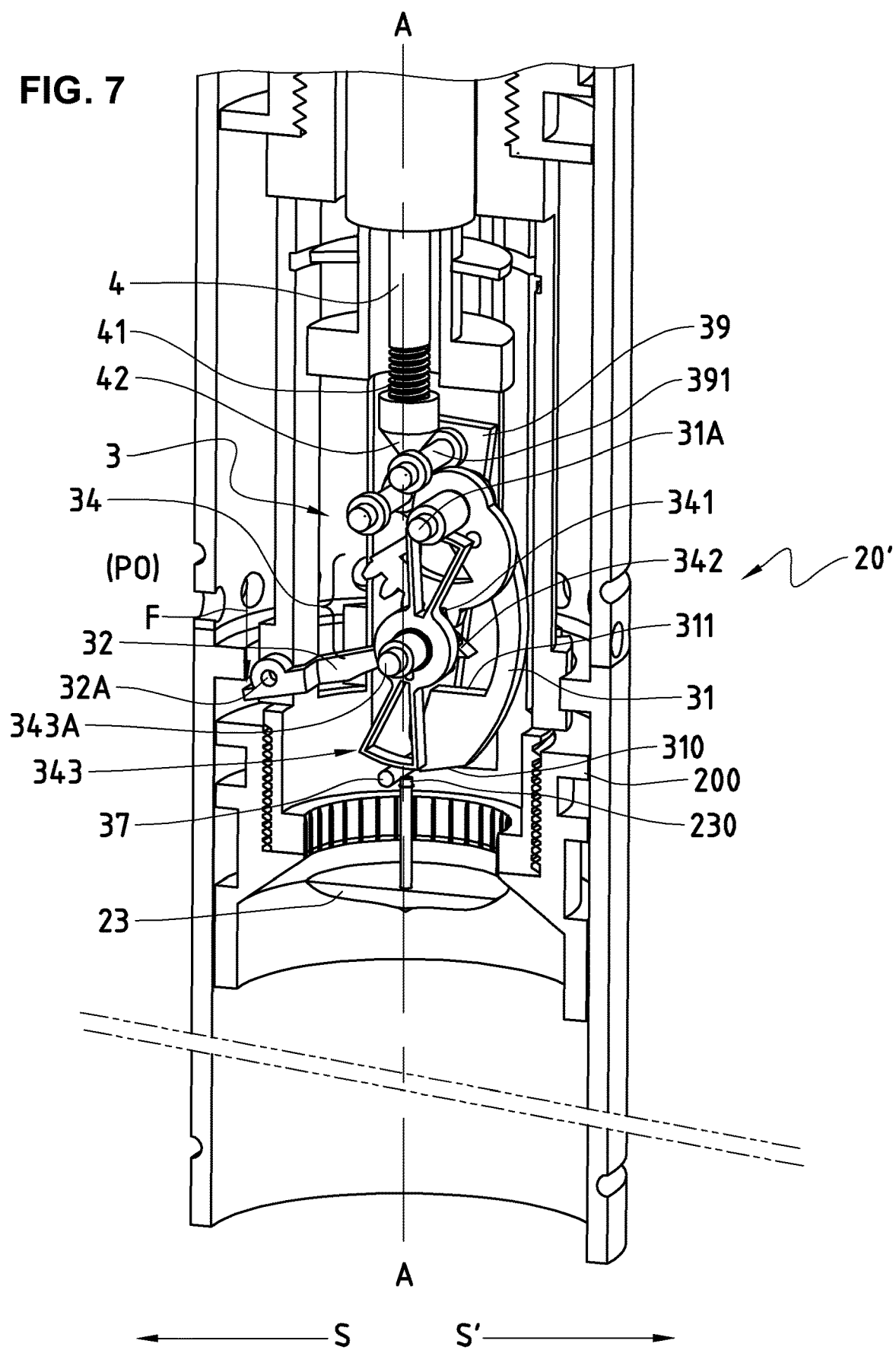
FIG. 7 is an illustration of a modified pendulum for the switching between the stance mode and the swing mode of the prosthesis according to a third preferred embodiment of the invention.

According to the preferred embodiment illustrated by FIGS. 5 to 7, it can be noted that the switching device 20 of the piston employed as damping mechanism 200 comprises functional elements similar to those of the standard switching system 20, namely a pendulum co-operating alternatively with, on the one hand, a counterweight in the first operating mode (M1), and, on the other hand, with the valve in the second operating mode (M2); nevertheless the modification of the structure of these elements gives them different physical properties altering the conditions for activation of the switching from stance mode, which is the operating mode by default, to swing mode, without however calling into question the necessity of being in a position of hyperextension P0 of the prosthesis to make such switching possible.

The same physical principle which applies to all these embodiments is to "delay" the pendulum's action on the valve when a step is taken such that its check valve function is only activated when the tibial part 102 has already tipped in the direction of walking S. Thus, the center of gravity of the pendulum at rest and suspended from the vertical is preferably offset, in different ways, slightly rearwards, in the opposite direction of walking S', with respect to the axis A-A of the piston, such that its functioning can only be activated preferably when a certain predetermined angle of inclination forwards, that is to say in the direction of walking S, is exceeded for the tibial part 102. Because of the angular offsetting between the piston and the tibial part 102, this corresponds in practice to a condition of exceeding another predetermined angle of inclination determined by the formula:

$$x > X1 = X2 + \Theta,$$

where x is the current angle of the tibial part 102 of the prosthesis 1 with respect to the ground, X1 a first predetermined oriented angle in the direction of walking and X2 a second predetermined oriented angle in the direction of walking, which is derived directly from the first.

In order to correspond to physical reality, in practice, the first predetermined oriented angle will preferably be between 0° and 5° degrees, and this angle will preferably be adjustable in order to be able to adapt as finely as possible to the movement of the wearer of the prosthesis. Nevertheless, it will be understood that other angular values are possible without departing from the scope of the present invention.

In the following, since the body of the piston and of numerous different constituent elements of the locking system 3 are identical for FIGS. 5, 6 and 7, all these elements common to these figures will not be described in detail for each of them FIG. 5 thus describes a preferred embodiment for the locking system 3 integrated in a modified switching system 20' of a common SNS piston, and which comprises a modified pendulum 31 of substantially tapered and arched shape, much easier to machine than the potatoid shape usually employed for such a pendulum. The modified pendulum 31 is mounted pivoting about a pivot axis 31A offset rearwards with respect to the axis A-A of the piston, that is to say in the opposite direction of walking S', such that its center of gravity is consequently offset and necessitates a more pronounced inclination of the piston forwards, that is to say in the direction of walking, so that it can fulfil its function as check valve for the valve 23.

As previously described with respect to FIG. 2, the piston still acts as damping mechanism 200 which still comprises a valve 23 equipped with a rod 230 at its upper end, co-operating with a stop portion 310 arranged on the lower end of the modified pendulum 31, while an inner support surface 311 is provided to allow the end of a counterweight, which takes the form here of a straight lever 32 pivoting about its pivot axis 32A arranged on the front of the piston, that is to say in the direction of walking S with respect to the axis A-A of the latter, to rest on a lower portion of the pendulum to lock it in a position where the return of the valve is never prevented. The modified switching mechanism 20' of the damping mechanism 200 being represented in a position of hyperextension P0 of the prosthesis, that is to say where the change of operating mode is able to be activated by reason of the raised position of the lever 32 owing to the action of the force F on its other end. In order to allow the swing movement of the lever 32, illustrated by the arrows, between its resting position and its release position, as is represented in FIG. 5, a clearance 312 is provided on the inner face of the modified pendulum 31, such that no additional accommodation is necessary beyond the volume of the piston.

As can be seen in FIG. 5, the modified pendulum 31 is moreover arranged at the end of a first articulated arm 33, whose pivot axis 33A is situated on the axis A-A of the piston, and whose position, offset rearwards in the opposite direction of walking S', can be adjusted with the aid of an adjustment device 4 comprising an adjustment screw 41 arranged along the axis A-A and which is connected, at its lower end, to a second articulated arm 36 whose pivot axis 36A is likewise situated on the axis A-A of the piston. The relative length of the different articulated arms—that is to say of the first articulated arm 33 and that of the second articulated arm 36—and the thread of the adjustment screw 41 are preferably configured such that the switching to the second operating mode M2, that is to say the swing mode of the prosthesis 1, can only be released starting from an inclination of the tibial part 102 of the prosthesis forwards in the direction of walking S by a few degrees. The adjustment can be performed continuously in a minimal range of values of angles of inclination determining the threshold of release, corresponding to the first predetermined oriented angle X1, which is preferably strictly positive to ensure the additional condition of safety sought, and preferably be between 0° and 5°. The preferred adjustment device 4 illustrated thus governs the value of the first predefined oriented angle (X1) as activation threshold for the switching to the swing mode by means of offsetting the pivot axis 31A of the modified pendulum 31 with respect to the axis of the piston. According to the illustrated embodiment, the relation between the value of offsetting with respect to the axis of the piston A-A in millimeters and the value of required additional inclination to allow the activation of the switching is not linear however; it has been noted, for example, that an offsetting of the axis of the pendulum 31A by 2.8 mm sets as a condition the value of the first predefined oriented angle X1 by +2° degrees, whereas an offsetting of the axis of the pendulum 31A by 3.8 mm sets as a condition the value of the first predefined oriented angle X1 by +5°. Thus we can therefore start with the principle that the adjustment is all the finer the closer to the vertical an inclination is adjusted, that being so at the start of the adjustment when the pivot axis 31A of the pendulum is practically situated on the axis of the piston A-A, and the granularity diminishing as one further adjusts the release threshold for switching.

Furthermore, in order to keep the stop portion 310 in blocking position vis-à-vis the rod 230 of the valve 23 even when the release threshold permitting passage to the swing mode has been surpassed, a stop to limit travel 37 is provided to limit the amplitude of pivoting of the modified pendulum 31 forwards, that is to say in the direction of walking S, and to thus ensure that it cannot assume a position where the return of the valve 23 would no longer be prevented once this threshold of inclination is passed; in effect this would then have as a consequence to re-switch the hinged connecting device 2 into the stance mode, which is evidently not desirable. Such a stop to limit travel 37 can also be useful in the case of any sudden movement forwards which would generate a powerful swing of the modified pendulum 31 in the direction of walking S and could bring it beyond the desired blocking position preventing the return of the valve 23 of the piston.

FIG. 6 represents a modified switching device 20' according to an implementation variant according to which the modified pendulum 31, instead of having a pivot axis 31A offset with respect to the axis of the piston A-A, as in FIG. 5, in order to offset the center of gravity of the latter rearwards—that is to say in the opposite direction of walking S'—now comprises a balourd, that is to say a weighted part 35. The technical effect obtained in terms of offsetting of the center of gravity of the pendulum is certainly the same; nevertheless no dynamic adjustment is now possible with such a variant such as represented. The geometric shape, the placement of the weighted part 35 on the pendulum and/or the intrinsic modification of the form of the pendulum, as well as the weight of this weighted part being able to influence this offsetting, it will be understood that a multitude of variants are possible without departing from the scope of the present invention. In order to provide a preliminary, even static, adjustment, and a certain subtlety in the adjustment granularity, weights of different value could be provided, however, and insertion locations on the modified pendulum 31.

Furthermore, because of the increase in the inertia of the modified pendulum 31, a second stop 38 is provided, in addition to the stop to limit travel 37, but this time to limit the amplitude of swing of the modified pendulum 31 rearwards, that is to say in the opposite direction of walking S'. This second stop 38 thus makes it possible to compensate for, or to minimize, the effects of inertia of the modified pendulum 31 in the context of a dynamic modelling, the release thresholds for the activation of the change of operating mode, that is to say the first predetermined oriented angle X1 of inclination of the tibial part, being otherwise determined by static balancing considerations.

FIG. 7 concerns another preferred embodiment for realization of the invention, still integrating the locking device 3 in the switching system 20 of an SNS piston, thus forming a modified switching system 20'. According to this variant, the modified pendulum 31 is mounted on an inclinable support 39, the position of which governs the radial offsetting of the position of its pivot axis 31A with respect to the axis of the piston 31, in a way similar to the previously described variant illustrated in FIG. 5, where a system of articulated arms was used to this effect. To carry out the adjustment, an adjustment device 4 of screw 41 type, arranged along the axis of the piston A-A, is still employed, but which is now equipped with a tapered pusher head 42 resting against an adjustment pin 391 integral with the support 39. Thus, when the pusher head 42 is moved downward, the support 39 is inclined rearwards, that is to say in the opposite direction of walking S', along with the pivoting axis of the modified pendulum 31.

Furthermore, the locking system 3 is now provided with a gearing mechanism 34 in order to obtain a gear ratio between the pivoting of a mobile 343, mounted in a way movable in rotation on the axis of rotation of the piston A-A, and that of the modified pendulum 31, in order to slow down the return thereof when it tends to be brought in position of blocking of the return of the valve. As illustrated in FIG. 7, the modified pendulum 31 is mounted in a way pivoting about its pivot axis 31A, but integral in rotation with a piece equipped with a first toothed portion 341, which meshes with a second toothed portion 342, which itself is integral in rotation with the mobile 343, whose axis of rotation 343A is placed here directly on the axis of the piston. The inertia of the mobile 343 is chosen preferably as being significantly greater than that of the modified pendulum 31, such that it is the displacement of the mobile 343 which drives that of the pendulum, and not the reverse; moreover, the gear ratio, for example 2:1 between the number of teeth of the second toothed portion 342 integral with the mobile 343 and that of the first toothed portion 341 integral with the modified pendulum 31 is chosen to give a leverage effect to the rotation of the modified pendulum 31, by reducing by as much the pivoting range of the latter according to the proportions of the gear ratio. By adjusting the parameters of the gearing, the desired first predetermined oriented angle X1 can thus be adjusted permitting the activation of the second operating mode M2, that is to say the passage from the stance mode to the swing mode.

It will be understood from the preceding detailed description that the embodiments are only given by way of example, without their being an exhaustive enumeration, to determine the scope of protection for the present invention. In particular, although presented according to a preferred variant as module able to be integrated in a conventional SNS piston, the solution according to the invention is equally compatible with the development of an integral system, including a new piston. Moreover, the advantageous features taken from described preferred embodiments could be taken alone or in combination, in particular as concerns the offsetting of the pivot axis 31A of the modified pendulum 31, the presence or not of a weighted part 35, as well as that of a gearing mechanism 34.

The invention claimed is:

1. Hinged connecting device for a prosthesis for a femoral amputee, the said prosthesis comprising:
    a femoral part adapted to end a thigh of the amputee;
    a tibial part adapted to replace a leg of the amputee;
    an intermediate knee part connecting the femoral part to the tibial part;
    a foot part adapted to replace a foot of the amputee, with a view to ensure taking support on a support surface;
said hinged connecting device being integrated in said intermediate knee part in such a manner as to ensure an articulated connection between said femoral part and said tibial part of said prosthesis between:
    a first position of hyperextension, in which said femoral part and said tibial part extend substantially one from the other, and
    a second position of maximal bending, in which said femoral part and said tibial part form a predetermined maximal flexion angle,
said hinged connecting device further comprising a damping mechanism adapted to counter a predetermined resistance at least during bending of said prosthesis, by replacing muscle groups usually used for this purpose, said damping mechanism being switchable between:
    a first operating mode, selected by default, in which a value of the resistance corresponds to a first maximum value, and
    a second operating mode, able to be actuated only in the first position of hyperextension, in which the resistance value corresponds to a second minimum value;
    said hinged connecting device further comprising a fully mechanical locking system designed to permit activation of said second operating mode only from a certain inclination of said tibial part corresponding to a first predetermined oriented angle with respect to a vertical direction in a direction of walking; and wherein said locking system is incorporated in a piston acting as said damping mechanism.

2. Hinged connecting device according to claim 1, said first predetermined oriented angle being greater than or equal to 0 in the direction of walking (S).

3. Hinged connecting device according to claim 1, said locking system comprising a modified pendulum of a modified switching system adapted to co-operate alternatively with a counterweight in the first operating mode, and with a valve of the piston in the second operating mode.

4. Hinged connecting device according to claim 3, wherein the modified pendulum is configured in such a way that the resistance of the damping device is locked in the first operating mode as long as an inclination of an axis of the piston does not exceed a second predetermined oriented angle with respect to the vertical direction derived directly from said first predetermined oriented angle as a function of an angle formed between said tibial part and said piston.

5. Hinged connecting device according to claim 3, wherein the modified pendulum comprises a weighted part shifting a center of gravity of the pendulum in a reverse direction of walking (S') with respect to an axis of the piston.

6. Hinged connecting device according to claim 3, wherein the modified pendulum is connected kinematically to a gearing system.

7. Hinged connecting device according to claim 3, wherein the modified pendulum has a pivot axis offset with respect to an axis of the piston.

8. Hinged connecting device according to claim 3, wherein the modified pendulum is of substantially arched shape and comprises a clearance on its inner surface in order to permit pivoting of the counterweight towards and from a support surface when the first operating mode is switched to the second operating mode.

9. Hinged connecting device according to claim 3, further comprising a stop to limit travel of the modified pendulum.

10. Hinged connecting device according to claim 1, further comprising an adjustment device for adjusting the value of the said first predetermined angle.

11. Hinged connecting device according to claim 10, said adjustment device acting upon a positioning of the pivot axis of a modified pendulum.

12. Hinged connecting device according to claim 11, said adjustment device comprising a screw actuating a system of articulated arms, one end of which bears said pivot axis of the modified pendulum.

13. Prosthesis comprising the hinged connecting device according to claim 1.

* * * * *